(12) United States Patent
Matsushita et al.

(10) Patent No.: US 7,132,243 B2
(45) Date of Patent: Nov. 7, 2006

(54) CLONAL EXPANSION OF T CELLS OF UNKNOWN SPECIFICITY AND IDENTIFICATION OF LIGAND RECOGNIZED BY THE CLONALLY EXPANDED T CELLS

(75) Inventors: Sho Matsushita, Kumamoto (JP); Toshihiro Nakashima, Kumamoto-ken (JP)

(73) Assignee: Juridical Foundation The Chemo-Sero-Therapeutic Research Institute, Kumamoto (JP)

( * ) Notice: Subject to any disclaimer, the term of this patent is extended or adjusted under 35 U.S.C. 154(b) by 347 days.

(21) Appl. No.: 09/962,445

(22) Filed: Sep. 26, 2001

(65) Prior Publication Data

US 2002/0192705 A1    Dec. 19, 2002

(30) Foreign Application Priority Data

Mar. 21, 2001  (JP) .............................. 2001-079621

(51) Int. Cl.
*G01N 33/53* (2006.01)
*G01N 33/566* (2006.01)
*C12N 5/08* (2006.01)

(52) U.S. Cl. ........................ 435/7.1; 435/7.2; 435/7.21; 435/325; 435/366; 435/372.3; 435/DIG. 2; 435/DIG. 14; 435/DIG. 15

(58) Field of Classification Search ................ 435/7.1, 435/7.2, 7.21, 325, 366, 372.3, DIG. 2, DIG. 14, 435/DIG. 15

See application file for complete search history.

(56) References Cited

OTHER PUBLICATIONS

Hiemstra et al., Proc. Natl. Acad. Sci. USA (Sep. 1999) vol. 94, pp. 10313-10318.*
Bruserud et al., Journal of Interferon and Cytokine Research, (2000), vol. 20, pp. 947-954.*
Pinilla et al., Current Opinion in Immunology 1999, 11:93-202.*
Matsushita et al., European Journal of Immunology 31(8): 2395-2402, (2001).*
Matsushita and Matsuoka, Eur. J. Immunol., 29:431-436, (1999).*
Tanaka et al., Human Immunology, 59: 343-351, (1998).*
Hemmer et al., Immunol. Today, (1998), vol. 19, pp. 163-168.*
Tana et al., Hum. Genet. (1998), vol. 43, 14-21.*
Y. Tanaka et al., J. Immunol., 162, pp. 7155-7161 (1999).
B. Hemmer et al., J. Exp. Med., 185, pp. 1651-1659 (1997).
S. Matsushita et al. J. Immunol., 158, pp. 5685-5691 (1997).
Y. Tanaka et al., Hum. Immunol., 59, pp. 343-351 (1998).
S. Matsushita et al., Eur. J. Immunol., 29, pp. 431-436 (1999).
Y. Chen et al., Hum. Immunol., 54, pp. 30-39 (1997).
S. Matsushita et al., J. Immunol., 138, pp. 109-115 (1987).

* cited by examiner

*Primary Examiner*—Mark Shibuya
(74) *Attorney, Agent, or Firm*—Birch, Stewart, Kolasch and Birch, LLP

(57) ABSTRACT

A process for clonally expanding T cells of unknown specificity and a process for identifying a peptide ligand recognized by said T cells are provided.

A process for clonally expanding T cells of unknown specificity which comprises co-culturing said T cells of unknown specificity with combinatorial randomized peptide library (Xn peptide library wherein n is a number of amino acids) consisted of peptides having a randomized amino acid sequence consisted of amino acid residues selected from nineteen kinds of naturally occurring amino acid other than cysteine, an interleukin, and major histocompatibility complex (MHC) class II antigen-expressing cells with DNA synthesis being suspended, said cells being derived from the individual where said T cells are obtained; and a process for identifying a peptide ligand recognized by the T cell clone of unknown specificity obtained by said process, which comprises determining proliferating activity of said T cell clone with Xn peptide library, in the presence of an interleukin and MHC class II antigen-expressing cells with DNA synthesis being suspended, said cells being derived from the individual where said T cells are obtained, to thereby determine a peptide sequence that can activate proliferation of T cells.

7 Claims, 5 Drawing Sheets

[Figure 1]
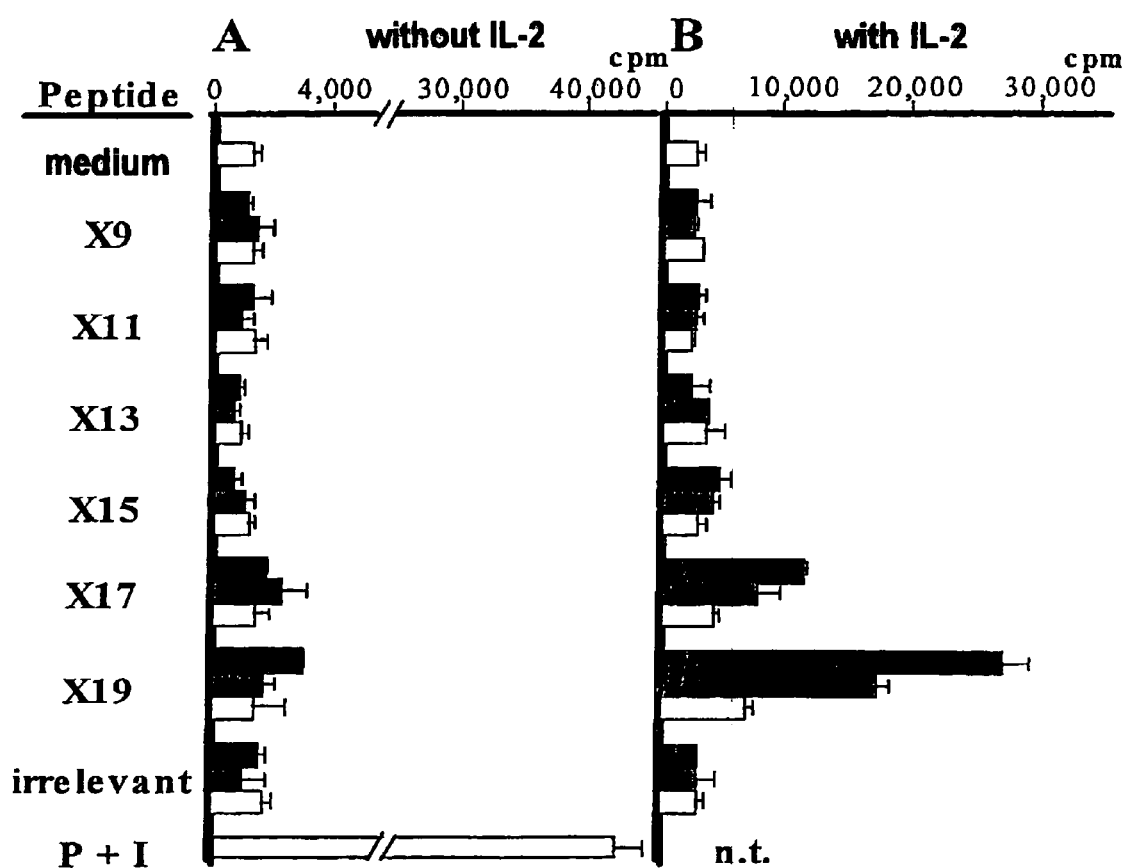

[Figure 2]
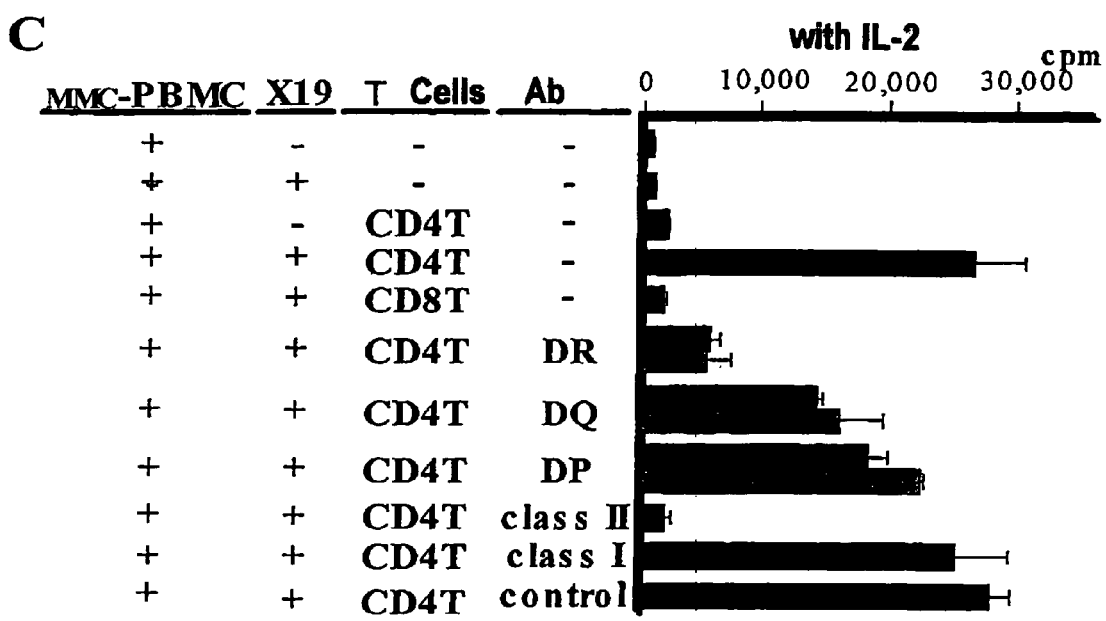

[Figure 3]
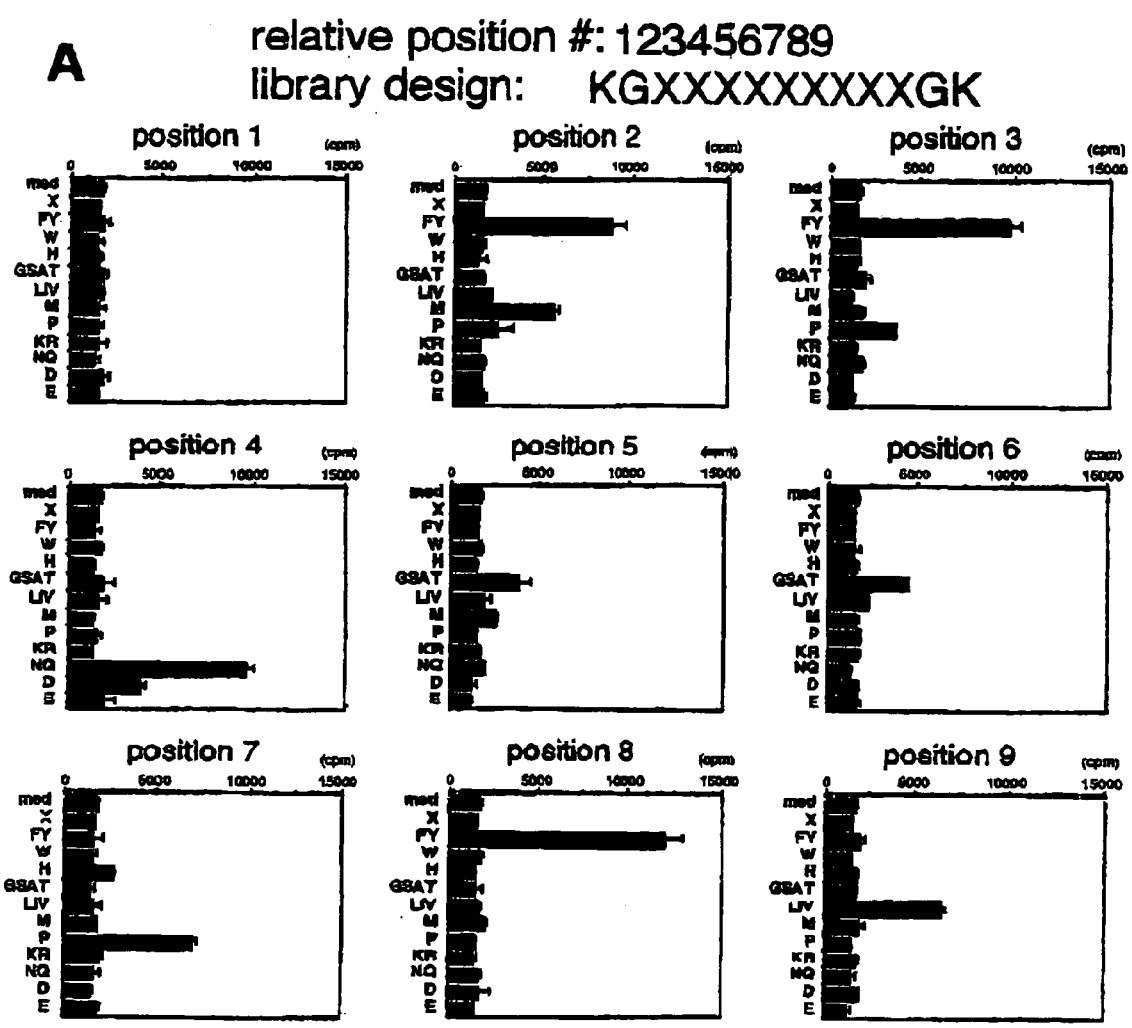

[Figure 4]
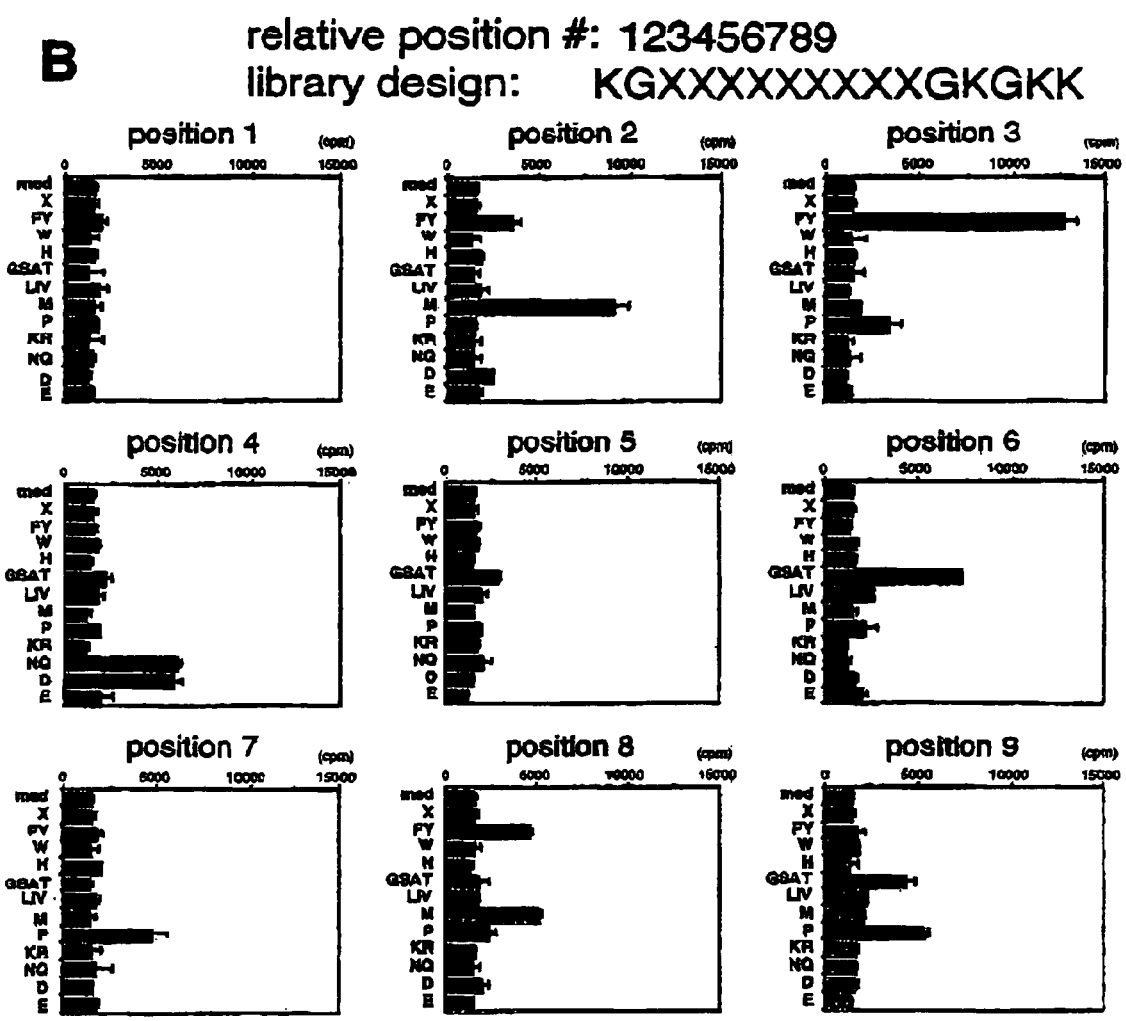

[Figure 5]
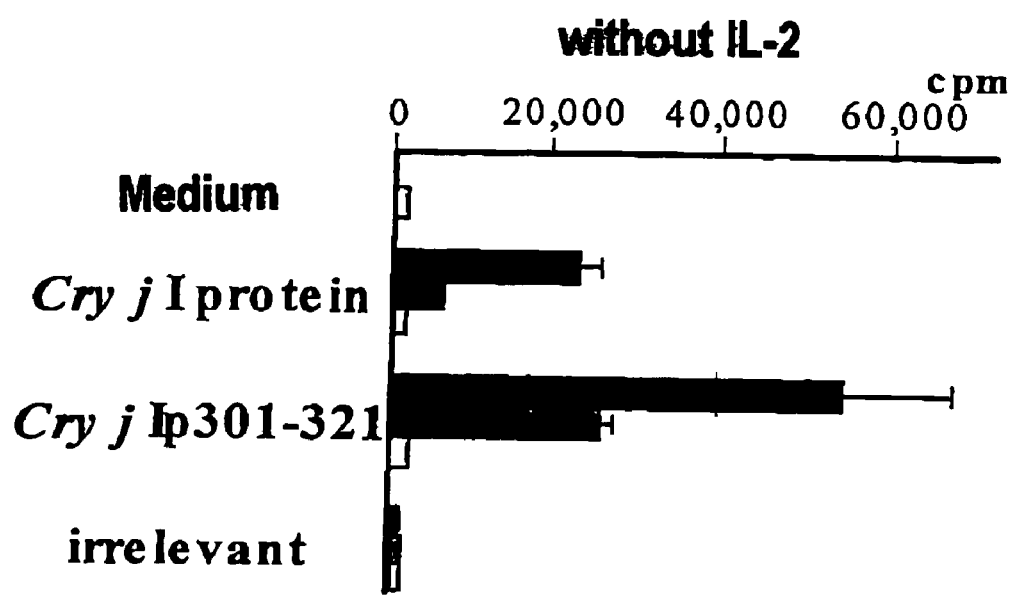

SEQUENCE LISTING

```
<160> NUMBER OF SEQ ID NOS: 15

<210> SEQ ID NO 1
<211> LENGTH: 13
<212> TYPE: PRT
<213> ORGANISM: Artificial Sequence
<220> FEATURE:
<223> OTHER INFORMATION: Synthetic X9-based peptide library
<221> NAME/KEY: UNSURE
<222> LOCATION: (3)..(11)
<223> OTHER INFORMATION: Xaa is any amino acid selected from nineteen
      kinds of naturally occurring amino acid other than cysteine

<400> SEQUENCE: 1

Lys Gly Xaa Xaa Xaa Xaa Xaa Xaa Xaa Xaa Xaa Gly Lys
 1               5                   10

<210> SEQ ID NO 2
<211> LENGTH: 16
<212> TYPE: PRT
<213> ORGANISM: Artificial Sequence
<220> FEATURE:
<223> OTHER INFORMATION: Synthetic peptide sequence
<221> NAME/KEY: UNSURE
<222> LOCATION: (3)..(11)
<223> OTHER INFORMATION: Xaa is any amino acid selected from nineteen
      kinds of naturally occurring amino acid other than cysteine

<400> SEQUENCE: 2

Lys Gly Xaa Xaa Xaa Xaa Xaa Xaa Xaa Xaa Xaa Gly Lys Gly Lys Lys
 1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Irrelevant synthetic peptide
```

-continued

```
<400> SEQUENCE: 3

Val Pro Ile Gln Arg Ala Val Tyr Gln Asn Val Val Asn Asn
 1               5                  10                  15

<210> SEQ ID NO 4
<211> LENGTH: 21
<212> TYPE: PRT
<213> ORGANISM: Artificial Sequence
<220> FEATURE:
<223> OTHER INFORMATION: Synthetic peptide Cry j I p301-321

<400> SEQUENCE: 4

Asp Val Phe Tyr Asn Gly Ala Tyr Phe Val Ser Ser Gly Lys Tyr Glu
 1               5                  10                  15

Gly Gly Asn Ile Tyr
            20

<210> SEQ ID NO 5
<211> LENGTH: 18
<212> TYPE: PRT
<213> ORGANISM: Homo sapiens

<400> SEQUENCE: 5

Ser Thr Pro Pro Pro Gly Thr Arg Val Arg Ala Met Ala Ile Tyr Lys
 1               5                  10                  15

Gln Ser

<210> SEQ ID NO 6
<211> LENGTH: 21
<212> TYPE: PRT
<213> ORGANISM: Homo sapiens

<400> SEQUENCE: 6

Ile Gly Arg Ile Ala Glu Cys Ile Leu Gly Met Asn Pro Ser Arg Asp
 1               5                  10                  15

Val His Asp Ala Ser
            20

<210> SEQ ID NO 7
<211> LENGTH: 14
<212> TYPE: PRT
<213> ORGANISM: Homo sapiens

<400> SEQUENCE: 7

Arg Ser Leu Arg Thr Val Thr Pro Ile Arg Met Gln Gly Gly
 1               5                  10

<210> SEQ ID NO 8
<211> LENGTH: 13
<212> TYPE: PRT
<213> ORGANISM: Homo sapiens

<400> SEQUENCE: 8

Pro Leu Phe Ser His Leu Gln Asn Glu Gln Trp Val Asp
 1               5                  10

<210> SEQ ID NO 9
<211> LENGTH: 18
<212> TYPE: PRT
<213> ORGANISM: Homo sapiens
```

-continued

<400> SEQUENCE: 9

Glu Tyr Lys Leu Val Val Gly Ala Gly Gly Val Gly Lys Ser Ala
1               5                   10                  15

Leu Thr

<210> SEQ ID NO 10
<211> LENGTH: 21
<212> TYPE: PRT
<213> ORGANISM: Homo sapiens

<400> SEQUENCE: 10

Leu Gln Asp Val Met Asn Ile Leu Leu Gln Tyr Val Val Lys Ser Phe
1               5                   10                  15

Asp Arg Ser Thr Lys
            20

<210> SEQ ID NO 11
<211> LENGTH: 13
<212> TYPE: PRT
<213> ORGANISM: Homo sapiens

<400> SEQUENCE: 11

Glu Tyr Ile Gln Gln Asn Gly Val Val Glu Glu Arg Ser
1               5                   10

<210> SEQ ID NO 12
<211> LENGTH: 17
<212> TYPE: PRT
<213> ORGANISM: Homo sapiens

<400> SEQUENCE: 12

Glu Glu Tyr Leu Ile Leu Ser Ala Arg Asp Val Leu Ala Val Val Ser
1               5                   10                  15

Lys

<210> SEQ ID NO 13
<211> LENGTH: 8
<212> TYPE: PRT
<213> ORGANISM: Yeast

<400> SEQUENCE: 13

Phe Pro Asp Ser Thr Pro Tyr Ile
1               5

<210> SEQ ID NO 14
<211> LENGTH: 8
<212> TYPE: PRT
<213> ORGANISM: Mycoplasma pneu

<400> SEQUENCE: 14

Phe Phe Asn Ser Gly Ala Phe Gly
1               5

<210> SEQ ID NO 15
<211> LENGTH: 8
<212> TYPE: PRT
<213> ORGANISM: Japanese cedar pollen

<400> SEQUENCE: 15

Phe Tyr Asn Gly Ala Tyr Phe Val
1               5

CLONAL EXPANSION OF T CELLS OF UNKNOWN SPECIFICITY AND IDENTIFICATION OF LIGAND RECOGNIZED BY THE CLONALLY EXPANDED T CELLS

The present invention relates to a process for clonal expansion of single T cells of unknown specificity by stimulation, proliferation and cloning of peripheral memory T cells of unknown specificity with combinatorial peptide library, and identification of a peptide ligand recognized by said clonally expanded T cells. The process of the present invention enables identification of epitopes recognized by T cells involved in autoimmune diseases or peptide ligands recognized by T cells associated with malignant tumors.

BACKGROUND OF THE INVENTION

It is commonly recognized that autoimmune diseases are provoked by activation of T cells reactive with self-antigens and cytokines or inflammatory mediators produced mainly by the activated T cells in turn damage the tissues. Thus, for treatment of autoimmune diseases, there have been attempts to suppress the activation of T cells reactive with self-antigens or to inhibit broadly and non-specifically the cytokines or the inflammatory mediators produced.

Recently, specific immunotherapies are expected to be the best therapy for autoimmune diseases. Once it becomes possible to identify peptide ligands recognized by every T cells at the peripheral, an antigenic epitope recognized by the T cells that are causing autoimmune diseases could be found out to lead to development of specific immunotherapies aimed at said etiologic T cells. For treatment of malignant tumors, it is also expected to develop specific immunotherapies wherein T cells that specifically attack tumor cells are chosen and activated. However, identification of antigens that are specific to patients and are recognized by T cells as well as determination of an amino acid sequence of said antigens has not yet been successfully achieved.

Much effort has been made for developing a method for identification of peptide ligands recognized by T cells. In case of identification of epitopes recognized by the previously reported T cell clones, a strategy has been employed wherein particular natural antigens to be anticipated were added during cloning of T cell and T cell clones responsive to said particular antigens were proliferated. This approach, however, is disadvantageous in that not T cell clones but those that recognize such particular antigens anticipated could be proliferated and if no T cells capable of recognizing said particular antigens are contained in the culture, then no proliferation of T cells could be obtained.

An alternative process for identifying peptide ligands recognized by cloned T cells have been reported (Tanaka, Y. et al., *J. Immunol.* 1999, 162: 7155–7161, "Identification of peptide superagonists for a self-K-ras-reactive CD4$^+$ T cell clone by use of combinatorial peptide libraries and mass spectrometry"; Hemmer, B. et al., *J. Exp. Med.* 1997, 185: 1651–1659, "Identification of high potency microbial and self ligands for a human autoreactive class II-restricted T cell clone").

However, as far as peripheral T cells of unknown specificity are concerned, clones per se could hardly be obtained to render it difficult to propagate T cells to a degree sufficient for testing. In order to obviate the difficulty, an attempt has been made to stimulate T cells with an immobilized anti-CD3 antibody in the presence of IL-2 but the long-term maintenance of T cells could not readily achieve. This is supposedly due to lack of physiological response of APC via APC-peptide-T cell interaction.

Thus, there is a need for developing a process for proliferating peripheral T cells of unknown specificity for cloning as well as for effective analysis of epitopes recognized by said T cells.

In the previous study, it was observed that some peptide partial agonists support T cell survival (Matsushita, S. et al., *J. Immunol.* 1997, 158: 5685–5691). It was also observed that an agonistic anti-CD29 antibody MAR4 increased the efficiency in establishing T cell clones from PBMC, both by suppressing antigen-driven activation-induced cell death and by enhancing the T cell proliferation, only in the presence of TCR/CD3-mediated stimulation (Tanaka, Y. et al., *Hum. Immunol.* 1998, 59: 343–351). Moreover, it was observed that culture supernatant of antigen-stimulated T cells in the presence of monocytes, increased the efficiency of cloning, when added to culture wells for limiting dilution.

Under the circumstances, the present inventors constructed combinatorial randomized peptide library and stimulated peripheral blood- or tissue-derived T cells with this library in the presence of an interleukin so that the T cells are proliferated and cloned. The isolated T cell clone is then analyzed for its epitope recognition to identify epitopes recognized by said clone by combinatorial assay with peptide library. Based on the identified peptide sequence, natural peptide ligands recognized by the isolated T cell clone can then be identified by pattern match search with data base of sequence.

SUMMARY OF THE INVENTION

In one aspect of the present invention, a process for clonally expanding T cells of unknown specificity is provided which comprises co-culturing T cells of unknown specificity with combinatorial randomized peptide library, an interleukin, and major histocompatibility complex (MHC) class II antigen-expressing cells with DNA synthesis being suspended, said cells being derived from the individual where said T cells are obtained, and optionally in the presence of anti-CD29 antibody having an agonist activity.

In another aspect of the present invention, a process for identifying epitopes or peptide ligands that are recognized by the thus clonally expanded T cell clone is provided, which comprises determining reactivity of the clonally expanded T cell clone of unknown specificity with combinatorial peptide library.

BRIEF DESCRIPTION OF THE DRAWINGS

FIG. 1 depicts proliferation of T cells cultured in the presence of Xn peptide libraries (closed bar, 250 μM; hatched bar, 62 μM; and open bar, 16 μM) or PMA (1 ng/ml) plus ionomycin (0.3 μM) without (A) or with (B) IL-2. All data are indicated as the mean value of triplicate determinations±standard error. n.t.: not tested.

FIG. 2 depicts proliferation of CD4T cells and CD8T cells in the presence of X19 peptide library and effect of anti-MHC antibody on T cell proliferation wherein a concentration of X19 peptide library is either 30 μg/ml (closed bar) or 10 μg/ml (hatched bar). All data are indicated as the mean value of triplicate determinations±standard error. DR: anti-HLA-DR antibody; DQ: anti-HLA-DQ antibody; DP: anti-HLA-DP antibody; class II: a mixture of anti-HLA-DR antibody, anti-HLA-DQ antibody and anti-HLA-DP antibody; class I: human anti-MHC class I antibody; and control: mouse IgG antibody.

FIG. 3 shows the analysis of ligand recognized by the T cell clone isolated from PBMC by positional scanning with X9-based combinatorial peptide library: Lys Gly Xa1 Xa2 Xa3 Xa4 Xa5 Xa6 Xa7 Xa8 Xa9 Gly Lys (SEQ ID NO: 1).

FIG. 4 shows the analysis of ligand recognized by the T cell clone isolated from PBMC by positional scanning with X9-based combinatorial peptide library: Lys Gly Xa1 Xa2 Xa3 Xa4 Xa5 Xa6 Xa7 Xa8 Xa9 Gly Lys Gly Lys Lys (SEQ ID NO: 2).

FIG. 5 shows proliferation reaction of the isolated T cell clone (19.6.47) with cedar pollen and the relevant synthetic peptide, which said clone was estimated to recognize. Purified Cry j I protein (closed bar: 50 μg/ml, hatched bar: 50 μg/ml, and open bar: 0.5 μg/ml), Cry j I p301–321 (closed bar: 250 μM, hatched bar: 25 μM, and open bar: 2.5 μM), and irrelevant (irrelevant peptide: Val Pro Ile Gln Arg Ala Val Tyr Gln Asn Val Val Val Asn Asn (SEQ ID NO: 3)).

DETAILED DESCRIPTION OF THE PREFERRED EMBODIMENTS

T cells to be clonally expanded by the process according to the present invention may be any T cells whose specificity is unknown that may be obtained from peripheral blood, organs, lymph nodes, etc.

"Xn peptide library" as used herein means peptide library consisted of peptides having a randomized amino acid sequence consisted of n naturally occurring amino acid residues other than cysteine wherein n represents an integer of 9 to 19, typically 9, 11, 13, 15, 17 and 19. The library may conveniently be constructed by a combinatorial randomized peptide synthesis but any synthetic process may also be employed insofar as it provides peptides having randomized naturally occurring amino acid residues other than cysteine.

Xn peptide library may also be constructed by purifying peptide library biologically expressed with *E. coli*, phage or yeast provided that the peptides have randomized sequences.

Among Xn peptide library used, the highest T cell-proliferating activity was observed for X17 and X19 with X19 having remarkable proliferating activity. Xn peptides are used at a concentration ranging from 1 to 1000 μM, preferably from 62 to 250 μM.

Interleukin for use in the process according to the present invention may be a combination of IL-4, IL-7, IL-9 and IL-15. IL-2 may also be used alone or together with the combination of IL-4, IL-7, IL-9 and IL-15.

MHC class II antigen-expressing cells used in the process according to the present invention may be peripheral blood mononuclear cells (PBMC), transformant cells genetically engineered to express MHC class II antigen, or immortalized B cells, derived from the individual where said T cells are obtained. The MHC class II antigen-expressing cells are previously treated with a cytostatic agent such as mitomycin C or radiated so that the DNA synthesis is suspended before they are applied to culture.

Preferably, anti-CD29 antibody having an agonist activity may be present in the culture so that T cells may be clonally expanded more efficiently and T cells reactive with Xn peptide library may be proliferated. The anti-CD29 antibody used may be any anti-CD29 antibody having an agonist activity that is prepared in a usual manner.

In accordance with the process of the present invention, T cell clone of unknown specificity can be expanded in a large scale. It was found that T cells expanded by the process of the present invention are exclusively CD4 positive T cells (hereinafter also referred to as "CD4 T cells"). It was also found that the CD4 T cells expanded by the process of the present invention were memory T cells.

The efficient method to propagate single T cells using Xn peptide library according to the present invention may be applicable to characterization of T cells of various specificities. This is because the antigenic activity of Xn peptide library on T cells indicates clonal variations which may allow particular T cell populations to grow more rapidly than others to lead to biased T cell population.

The present invention also provides a process for identifying epitopes or peptide ligands recognized by the T cell clone of unknown specificity that was expanded by the process of the present invention.

The process comprises performing a positional scanning for the expanded T cell clone with Xn-based peptide library in the presence of IL-2 and MHC class II antigen-expressing cells with DNA synthesis being suspended, said cells being derived from the individual where said T cells are obtained, wherein those amino acid residues at each position within Xn peptide that exert activity to activate proliferation of T cells are selected to determine a peptide sequence that can activate proliferation of T cells.

Xn-based peptide library wherein n represents an integer may be used in the process of the invention and n is suitably determined depending on T cell clone of interest with the integer of 9 being preferred (X9). For example, X9-based peptide library such as Lys Gly Xa1 Xa2 Xa3 Xa4 Xa5 Xa6 Xa7 Xa8 Xa9 Gly Lys (SEQ ID NO: 1) or Lys Gly Xa1 Xa2 Xa3 Xa4 Xa5 Xa6 Xa7 Xa8 Xa9 Gly Lys Gly Lys Lys (SEQ ID NO: 2) may be used wherein Xa1 to Xa9 is a randomized amino acid residue selected from any naturally occurring amino acid other than cysteine.

The peptide sequence determined by the process as described above is the peptide ligand recognized by the T cell clone. To What natural peptide this peptide ligand corresponds may be determined by a pattern match search. Thus, the peptide ligand recognized by T cell clone of unknown specificity may be identified.

The present invention is explained in more detail by means of Examples but it should not be construed to be limited thereto.

EXAMPLE 1

Synthesis of Peptide Library

X19 peptide library was prepared by the Fmoc peptide synthesis using a 96-well peptide synthesizer Model SRM96A (Shimadzu Corp., Kyoto, Japan). For randomized peptide library, an equimolar mixture of Fmoc-L-amino acids of nineteen kinds of naturally occurring amino acids other than cysteine was reacted twice for coupling for each binding site. Combinatorial randomized peptide library, upon completion of coupling reaction of amino acids, was cleaved from the resin with 2-methylindole, precipitated with ice-cooled anhydrous ethyl ether and washed five times. Precipitates of peptides were dried under nitrogen atmosphere, dissolved in trifluoroacetic acid, precipitated with ethyl ether and again dried. The prepared peptides were dissolved in 50% acetonitrile containing 0.01 N HCl, and lyophilized. After lyophilization, the weighed peptides were dissolved at 50 mM in anhydrous dimethylsulfoxide, calculating a mean molecular weight of an amino acid as 110, and stored at −80° C. For use in culture, the peptide solution was diluted to 1 mM with the culture medium, centrifuged to remove precipitates, and was subject to sterile filtration with a filter of 0.45 μm.

EXAMPLE 2

Analysis of Peptide Library

The lyophilized preparation of the synthesized X19 combinatorial randomized peptide library was dissolved in 100 μL distilled water and centrifuged to remove precipitates. An amino acid composition analysis was performed for the X19 combinatorial randomized peptide library, which has previously been HCl-hydrolyzed for 21 hours, by reacting 20 μL the sample with 20 μL a reagent and 60 μL buffer, followed by HPLC of 20 μL of the reaction mixture.

The analysis proved that the peptides contained Asp+Asn 10.7 pmol (1.8%), Ser 43.0 pmol (7.2%), Glu+Gln 58.8 pmol (9.8%), Gly 68.5 pmol (11.4%), His 22.1 pmol (3.7%), Arg 5.9 pmol (1.0%), Thr 34.0 pmol (5.6%), Ala 63.5 pmol (10.5%), Pro 13.5 pmol (2.3%), Tyr 38.5 pmol (6.4%), Val 84.2 pmol (14.0%), Met 31.1 pmol (5.1%), Lys 45.9 pmol (7.6%), Ile 8.9 pmol (1.5%), Leu 66.1 pmol (11.0%), and Phe 3.8 pmol (0.7%). Thus, except for tryptophan that is not subject to analysis by this procedure, it was confirmed that all of the eighteen kinds of amino acids were contained roughly equally.

Then, the amino acid sequence up to the third from the N-terminus of the synthesized X19 combinatorial randomized peptide library was determined by Edman degradation procedure using Protein Sequencer Model 1492 (Applied Biosystems). As a result, it was confirmed that every position up to the third from the N-terminus was occupied randomly with any of the nineteen kinds of amino acid residues.

EXAMPLE 3

Mitomycin C Treatment of Peripheral Blood Mononuclear Cells (PBMC)

Peripheral blood mononuclear cells (PBMC) 5 to 10×10$^6$ cells/ml were cultured in a culture medium containing 2 mM L-glutamine, 100 U/ml penicillin, 100 μg/ml streptomycin and 10% heat-inactivated self plasma in RPMI 1640 medium (Gibco, Grand Island, N.Y.), supplemented with 20 μg/ml mitomycin C (Sigma) for 2 hours while stirring. After washing twice with RPMI 1640 medium, the cells were cultured in the culture medium for additional 3 to 5 hours. The cells were recovered, and washed twice with RPMI 1640 medium for use in the subsequent study.

EXAMPLE 4

Effects of the Peptide Length on Proliferating Activity to T Cells

For estimating effects of the peptide length on the T cell-proliferating activity, X9, X11, X13, X15, X17, and X19 peptide libraries were prepared each consisted of peptides having randomized amino acid sequence consisted of 9, 11, 13, 15, 17 or 19 amino acid residues in length, respectively.

1.5×10$^5$ cells/well PBMC from healthy adults were incubated in the presence of either of X9, X11, X13, X15, X17, or X19 peptide library at 16, 62 or 250 μM, or irrelevant peptide (Val Pro Ile Gln Arg Ala Val Tyr Gln Asn Val Val Val Asn Asn (SEQ ID NO: 3)) as a control or a combination of 1 ng/ml phorbol 12-myristate 13-acetate (PMA) and 0.3 mM ionomycin as a positive control, or a medium alone to determine the proliferative response of PBMC.

The cells were incubated either with or without IL-2. For the group with IL-2, it was added at Day 4. For all the groups, $^3$H thymidine was added at Day 6. When IL-2 was not added to the culture, no remarkable proliferative response was observed except for X17 and X19 where a weak proliferative response was exhibited at a higher concentration of the peptides as shown in FIG. 1A. With addition of IL-2, however, longer peptides such as X19 exhibited a potent proliferative response in a concentration-dependent manner (FIG. 1B).

It was also revealed that a subpopulation of T cells having the proliferative response was CD4 T cells (FIG. 2). The proliferative response was suppressed by adding monoclonal antibodies against human MHC class II (i.e. anti-HLA-DR antibody, anti-HLA-DQ antibody and anti-HLA-DP antibody) in a dose-dependent manner. Among these three antibodies, the effect of the anti-HLA-DR antibody was highest. Additive effects were observed when these monoclonal antibodies at saturating concentrations were added in admixture. No suppression of the proliferative response was observed with antibodies against MHC class I.

EXAMPLE 5

Effect of X19 Peptide Library on Proliferative Response in Various Human T Cell Clones For investigating whether X19 peptide library is capable of stimulating CD4 T cells of various specificities, mitomycin C-treated PBMC, human CD4 T cell clones of various specificities and IL-2 were co-incubated in the presence or absence of X19 peptide library.

Human CD4 T cell clones examined in this study included OT1.1 (DP5 restriction; recognition of p53pl53–165 peptide); T31.1 (DP5 restriction; recognition of TEL/AML-1 peptide); DT13.2 (DQ6 restriction; recognition of DerfIp18–31 peptide); SK2.11 (DQ6 restriction; recognition of AchRp75–87 peptide); 29.28.1 (DR8 restriction; recognition of Rasp3–20 peptide); 29.15.2 (DR51 restriction; recognition of Rasp3–20 peptide); MK20.2 (DR53 restriction; recognition of GADp111–131 peptide); HY6.22 (DR4 restriction; recognition of DerfIp82–94 peptide); YT15.1 (DR15 restriction; recognition of BCGap84–100 peptide); SF36.16 (DR4 restriction; recognition of BCGap84–100 peptide); BC20.7 (DR14 restriction; recognition of BCGap84–100 peptide); BC33.5 (DR14 restriction; recognition of BCGap84–100 peptide); and BC42.1 (DR14 restriction; recognition of BCGap84–100 peptide).

Each of the human T cell clones was weakly stimulated with radiated corresponding autologous PBMC in the presence of 50 U/ml human recombinant IL-2 and the endogenous peptides recognized by each of the human T cell clones. 2×10$^4$ cells/well test T cell clone were incubated in 96-well flat bottom culture plate in a culture medium containing 2 mM L-glutamine, 100 U/ml penicillin, 100 μg/ml streptomycin and 10% heat-inactivated self plasma in RPMI 1640 medium, supplemented with 20 U/ml human recombinant IL-2 and 1×10$^5$ cells/well autologous PBMC treated with mitomycin C, in the presence or absence of 250 μM X19 peptide library. Each clone was incubated for 72 hours wherein 1 μCi/well [$^3$H]-thymidine was added for the last 16 hours to estimate the effect of X19 peptide library on the enhancement of proliferative response of various human T cell clones. The results are shown in Table 1 which indicates [$^3$H]-thymidine incorporation after a 3-day culture determined in triplicate. In Table 1, mean cpm values are shown and standard error was less than 20%.

As is clear from Table 1, X19 peptide library induced proliferative response of T cell clones with variable degrees of agonism with one exception (HY6.22) The induction of proliferative response was observed in the presence of X19 peptide library and IL-2 for those T cell clones having the same HLA restriction but distinct specificities like between OT1.1 and T31.1 clones. The induction of proliferative response was also observed in the presence of X19 peptide library and IL-2 for those T cell clones recognizing the same peptide but having distinct HLA restriction like between 29.28.1 and 29.15.2 or between YT15.1, SF36.16 and BC20.7. Moreover, proliferative response was also induced in the presence of X19 peptide library and IL-2 in those T cell clones recognizing the same peptide and having the same HLA restriction but with distinct Vβ chains like between BC20.7, BC33.5 and BC42.1, demonstrating that superantigen-like effects of X19 peptide library is unlikely.

TABLE 1

| Clone | Wild-type ligand (sequence) | HLA (Vβ) | Reactivity to IL-2 | IL-2 + X19 |
|---|---|---|---|---|
| OT1.1 | p53p153–165 (STPPPGTRVRAMAIYKQS) | DP5 | 2,338 cpm | 4,981 |
| T31.1 | TEL/AML-1 (IGRIAECILGMNPSRDVHDAS) | DP5 | 1,312 | 3,855 |
| DT13.2 | Der f Ip18–31 (RSLRTVTPIRMQGG) | DQ6 | 1,927 | 3,096 |
| SK2.11 | AchRp75–87 (PLFSHLQNEQWVD) | DQ6 | 2,264 | 15,539 |
| 29.28.1 | Rasp3–20 (EYKLVVVGAGGVGKSALT) | DR8 | 1,502 | 5,683 |
| 29.15.2 | Rasp3–20 (EYKLVVVGAGGVGKSALT) | DR51 | 1,280 | 4,771 |
| MK20.2 | GADp111–131 (LQDVMNILLQYVVKSFDRSTK) | DR53 | 3,443 | 13,607 |
| HY6.22 | Der f Ip82–94 (EYIQQNGVVEERS) | DR4 | 2,005 | 2,196 |
| YT15.1 | BCGap84–100 (EEYLILSARDVLAVVSK) | DR15 | 1,729 | 3,820 |
| SF36.16 | BCGap84–100 (EEYLILSARDVLAVVSK) | DR4 | 2,407 | 6,238 |
| BC20.7 | BCGap84–100 (EEYLILSARDVLAVVSK) | DR14 (13.3) | 1,421 | 4,395 |
| BC33.5 | BCGap84–100 (EEYLILSARDVLAVVSK) | DR14 (6.1) | 3,201 | 6,626 |
| BC42.1 | BCGap84–100 (EEYLILSARDVLAVVSK) | DR14 (5.4) | 1,914 | 7,727 |

EXAMPLE 6

Preparation of Human Peripheral T Cell Subpopulations

Peripheral T cell subpopulations were prepared using Stemsep Kits (StemCell Technologies Inc., Vancouver). PBMC were freshly prepared from healthy adult donors using Ficoll-Paque, and then incubated with magnetic particles bound with a cocktail of antibodies against CD8, CD14, CD16, CD19, CD56 and glycophorin A, for the separation of CD4 T cells. The antibody-bound cells were removed with a magnetic column to prepare a subpopulation of CD4 positive T (CD4 T) cells. It was proved that the isolated CD4 T cells was >95% CD4 positive.

For preparation of memory and naive T cells, anti-CD45RA and anti-CD45RO antibodies were added to the above antibody mixture, respectively.

EXAMPLE 7

Investigation of Optimum Conditions for Efficient Proliferative Response of CD4 T Cells To all microculture wells in Terasaki plates (Sumitomo Bakelite, Tokyo), $3 \times 10^4$ cells/well mitomycin C-treated PBMC were added. CD4 T cells were separated from PBMC and added to the culture wells at one cell/well.

To the culture wells were added 250 μM X19 peptide library, 50 U/ml IL-2, 10 U/ml IL-4, 50 U/ml IL-7, 50 U/ml IL-9, 1 ng/ml IL-15, and 2.5 μg/ml anti-CD29 MAR4, in various combinations. On Day 7 after initiation of culture, well were microscopically examined for proliferative responses. Growing microcultures were fed with mitomycin C-treated PBMC, X19 peptide library and IL-2 in 96-well plates for seven days and subjected to proliferation assay with IL-2 and X19 peptide library. Wells with stimulation index (cpm with IL-2 plus X19 peptide library/cpm with IL-2 only) of more than 2.0 were considered to be X19 reactive. The results are shown in Table 2 wherein one culture group consisted of 120 culture wells in triplicate and the mean number of culture wells is indicated. Standard error was <25%.

In Experiment 1, various combinations of interleukins together with X19 peptide library were tested for their effect on proliferative response of CD4 T cells. It was found that a combination of IL-4, IL-7, IL-9 and IL-15 together with X19 peptide library could enhance most effectively the proliferative response of CD4 T cells and X-19 reactivity. Although IL-15 alone did not exhibit any marked enhancing effect, clonal expansion of T cells was less efficient when IL-2 was used instead of IL-15, in the combination with IL-4, IL-7 and IL-9.

Experiment 2 was performed wherein anti-CD29 antibody having an agonist activity was added to the culture together with the above combination of interleukins to thereby further enhance the proliferative response of CD4 T cells, especially X-19 reactive CD4 T cells.

Although some of the T cells did not show X19 peptide library-induced proliferative responses, culture in the absence of X19 peptide library exhibited a marked decrease in positive wells, demonstrating that the effect depends on antigenic stimuli via TCR/CD3.

In Experiment 3, subpopulation of CD4 T cells that were subject to proliferative response was investigated to prove that CD45RA$^-$ memory CD4 T cells were clonally expanded in response to the stimulation but not CD45RO$^-$ naive CD4 T cells.

TABLE 2

| | | | | Number of culture wells (per 120) | |
|---|---|---|---|---|---|
| CD4T | X19 | IL- | Anti-CD29 | Growing on d7 | X19-reactive |
| Exp. 1 | | | | | |
| + | + | — | − | 0.6 | 0 |
| + | + | 4, 7, 9 | − | 4.0 | 1.6 |
| + | + | 2 | − | 4.3 | 1.0 |
| + | + | 15 | − | 1.0 | 0.3 |
| + | + | 2, 15 | − | 3.0 | 1.3 |
| + | + | 4, 7, 9, 2 | − | 4.0 | 1.3 |
| + | + | 4, 7, 9, 15 | − | 8.6 | 2.6 |
| + | + | 4, 7, 9, 2, 15 | − | 4.6 | 1.0 |

TABLE 2-continued

| CD4T | X19 | IL- | Anti-CD29 | Number of culture wells (per 120) | |
|---|---|---|---|---|---|
| | | | | Growing on d7 | X19-reactive |
| Exp. 2 | | | | | |
| + | + | 4, 7, 9, 15 | − | 10.3 | 2.6 |
| + | + | 4, 7, 9, 15 | + | 10.0 | 8.3 |
| + | − | 4, 7, 9, 15 | + | 3.0 | 1.6 |
| − | + | 4, 7, 9, 15 | + | 0 | 0 |
| Exp. 3 | | | | | |
| memory | + | 4, 7, 9, 15 | + | 18.0 | 15.3 |
| naive | + | 4, 7, 9, 15 | + | 1.6 | 0.6 |

EXAMPLE 8

Identification of Peptide Ligand Recognized by Cloned T Cells

For identifying peptide ligands recognized by the T cell clone obtained directly from PBMC in Example 7, two sets of X9-based combinatorial peptide libraries that carry distinct flanking residues on their C-terminal moieties, Lys Gly Xa1 Xa2 Xa4 Xa5 Xa6 Xa7 Xa8 Xa9 Gly Lys (SEQ ID NO: 1) and Lys Gly Xa1 Xa2 Xa4 Xa5 Xa6 Xa7 Xa8 Xa9 Gly Lys Gly Lys Lys (SEQ ID NO: 2), were synthesized wherein Xa1 to Xa9 represents a randomized amino acid residue selected from nineteen kinds of any naturally occurring amino acid other than cysteine. Glycine residues were inserted flanking the X9 moiety to minimize steric hindrance around the P1 and P9 pocket of class II MHC and lysine(s) was inserted adjacent to the glycine residue to increase the solubility of the libraries.

These two sets of libraries were examined for their proliferation-inducing activity on the T cell clone. Each of the peptide libraries was added at a concentration of 250 μM and the activity was assessed in the presence of IL-2 (20 U/ml) and mitomycin C-treated PBMC ($1.0 \times 10^5$ cells/well).

As a result, it was found that these T cell clones showed heterogeneous and scattered proliferation patterns against these two X9-based combinatorial peptide libraries in an IL-2-dependent manner. The patterns obtained with 19.6.47 T cells established directly from PBMC are shown in FIGS. 3 and 4 wherein all data are shown as the mean value of duplicate determinations±standard error.

As is clear from FIG. 3, in case of X9-based combinatorial peptide library, Lys Gly Xa1 Xa2 Xa4 Xa5 Xa6 Xa7 Xa8 Xa9 Gly Lys, Tyr, Phe and Met at relative position 2, Tyr, Phe and Pro at relative position 3, Asn Gln and Asp at relative position 4, Gly, Ser, Ala and Thr at relative positions 5 and 6, Pro at relative position 7, Tyr and Phe at relative position 8, and Leu, Ile and Val at relative position 9, were effective for induction of proliferation.

Also as is clear from FIG. 4, similar results were obtained in case of the library, Lys Gly Xa1 Xa2 Xa4 Xa5 Xa6 Xa7 Xa8 Xa9 Gly Lys Gly Lys Lys, except that not only Tyr and Phe but also Met at relative position 8, and only small residues such as Gly, Ser, Ala, Thr and Pro at relative position 9 induced proliferation. It might be the C-terminal flanking residues differing between these two libraries that affected peptide conformation to lead to distinct recognition patterns by TCR (Matsushita, S. et al., *Eur. J. Immunol.*, 1999, 29: 431–436; Chen, Y.-Z. et al., *Hum. Immunol.*, 1997, 54: 30–39).

Taken together the above results, it was estimated that peptide ligands recognized by the T cell clone would be among the possible combinations of the following amino acid residues:

Xa2: Tyr, Phe and Met

Xa3: Tyr, Phe and Pro

Xa4: Asn Gln and Asp

Xa5: Gly, Ser, Ala and Thr

Xa6: Gly, Ser, Ala and Thr

Xa7: Pro

Xa8: Tyr, Phe and Met

Xa9: Leu, Ile, Val, Pro, Gly, Ser, Ala and Thr.

Pattern-match search was performed with SWISS-PLOT and TrEMBL wherein peptide ligand candidates that matched amino acids at 7–8 positions out of 8 positions were searched. As shown in Table 3 below, three non-autologous sequences were hit.

TABLE 3

| | Amino acid sequence | | | | | | | |
|---|---|---|---|---|---|---|---|---|
| | Xa2 #1 | Xa3 #2 | Xa4 #3 | Xa5 #4 | Xa6 #5 | Xa7 #6 | Xa8 #7 | Xa9 #8 |
| Mannosyl-transferase (Yeast) | $^{144}$Phe | Pro | Asp | Ser | Thr | Pro | Tyr | Ile$^{151}$ |
| SGAT homologue (Mycoplasma pneu.) | $^{462}$Phe | Phe | Asn | Ser | Gly | Ala | Phe | Gly$^{469}$ |
| Cry j I (Japanese cedar pollen) | $^{303}$Phe | Tyr | Asn | Gly | Ala | Tyr | Phe | Val$^{310}$ |

Note: #1: Tyr, Phe, Met; #2: Tyr, Phe, Pro; #3: Asn Gln, Asp; #4: Gly, Ser, Ala, Thr; #5: Gly, Ser, Ala, Thr; #6: Pro; #7: Tyr, Phe, Met; #8: Leu, Ile, Val, pro, Gly, Ser, Ala, Thr.

The donor of 19.6.47 T cells suffered from hay fever of Japanese cedar pollen and said T cells were established during heavy pollination season. In this respect, a major allergen of Japanese cedar pollen (*Cryptomeria japonica* I; Cry j I) among the three non-autologous peptides shown in Table 3 was considered to be a possible peptide ligand recognized by said T cell clone. Thus, a synthetic peptide Cry j I p301–321 (Asp Val Phe Tyr Asn Gly Ala Tyr Phe Val Ser Ser Gly Lys Tyr Glu Gly Gly Asn Ile Tyr (SEQ ID NO: 4)) and purified Cry j I protein were examined for their reactivity with the 19.6.47 T cells. A major allergen of Japanese cedar (*Cryptomeria japonica*) pollen was purified as described in Matsushita, S. et al., *J. Immunol.*, 1987, 138: 109–115.

The 19.6.47 T cells were cultured with radiated (45 Gy) PBMC either in the presence of purified Cry j I protein (50, 5.0 or 0.5 mg/ml), Cry j I p301–321 peptide (250 mM, 25 mM or 2.5 mM) or irrelevant peptide.

As shown in FIG. 5, the 19.6.47 T cells reacted not only with the synthetic peptide Cry j I p301–321 but also with purified Cry j I protein in a concentration dependent manner. As such, it was considered that the 19.6.47 T cells recognized in vivo the peptide p302–310 of Japanese cedar pollen as a natural ligand.

As stated above, peripheral CD4 memory T cells can be clonally expanded with X19 peptide library in accordance with the present invention. The peptide ligands or epitopes for said T cells may also be identified by combinatorial peptide libraries.

The present invention enables determination of antigenic peptide sequence for T cells of unknown specificity derived from peripheral blood or tissues which hitherto could have not identified. More specifically, the present invention enables identification of epitopes recognized by T cells involved in autoimmune diseases or peptide ligands recognized by CD4 T cells having the anti-tumor activity through clonal expansion of memory T cells of unknown specificity and identification of peptide ligands recognized by said T cells. The physiological T-APC interactions mediated by Xn peptide combinatorial library may have provided a microenvironment essential for T cells to proliferate, which cannot be achieved by conventional methods using, for example, anti-CD3 antibody.

Based on the identified peptide ligands, natural ligands recognized by T cells may also be identified or analogized. This may lead to a development of specific immunotherapies against autoimmune diseases or tumor immunotherapies against malignant tumors. The process of the present invention may also be effective means for identifying infection-protecting peptides against infectious diseases.

What is claimed is:

1. A process for clonally expanding CD4$^+$ memory T cells of unknown specificity for particular antigens, which comprises the steps of:
   obtaining CD4$^+$ memory T cells of unknown specificity for particular antigens, from a subject;
   co-culturing said CD4$^+$ memory T cells of unknown specificity with (i) a combinatorial randomized peptide library, X19, consisting of peptides having a randomized amino acid sequence of nineteen naturally occurring amino acids other than cysteine wherein the combinatorial randomized peptide library, X19, peptides exhibit agonistic activity toward T cells,
   (ii) interleukin, wherein said interleukin comprises IL-2, a combination of IL-4, IL-7, IL-9 and IL-15, or a combination of IL-2, IL-4, IL-7, IL-9 and IL-15,
   (iii) major histocompatibility complex (MHC) class II antigen-expressing cells with DNA synthesis being suspended, wherein said MHC class II antigen-expressing cells are also derived from the subject, and
   (iv) in the presence of anti-CD29 antibody having an agonist activity;
   so as to clonally expand said CD4$^+$ memory T cells of unknown specificity for particular antigens.

2. The process of claim 1, wherein a concentration of peptides in said combinatorial randomized peptide library is 1 to 1000 μM.

3. The process of claim 2, wherein a concentration of peptides in said combinatorial randomized peptide library is 62 to 250 μM.

4. The process of claim 1, wherein said interleukin is IL-2.

5. The process of claim 1, wherein said interleukin is a combination of IL-4, IL-7, IL-9 and IL-15.

6. The process of claim 1, wherein said interleukin comprises a combination of IL-2, IL-4, IL-7, IL-9 and IL-15.

7. The process of claim 1, wherein said MHC class II antigen-expressing cells are selected from the group consisting of peripheral blood mononuclear cells, transformant cells genetically engineered to express MHC class II antigen, and immortalized B cells.

* * * * *